(12) United States Patent
Carbaugh et al.

(10) Patent No.: US 9,109,405 B2
(45) Date of Patent: Aug. 18, 2015

(54) GAS HANDLER, RISER ASSEMBLY, AND METHOD

(71) Applicant: Hydril USA Manufacturing LLC, Houston, TX (US)

(72) Inventors: William L. Carbaugh, Humble, TX (US); Leonard G. Childers, Houston, TX (US); John R. LeBlanc, Houston, TX (US)

(73) Assignee: Hydril USA Distribution LLC, Houston, TX (US)

( * ) Notice: Subject to any disclaimer, the term of this patent is extended or adjusted under 35 U.S.C. 154(b) by 256 days.

(21) Appl. No.: 13/836,025

(22) Filed: Mar. 15, 2013

(65) Prior Publication Data

US 2013/0206422 A1   Aug. 15, 2013

Related U.S. Application Data

(62) Division of application No. 12/956,218, filed on Nov. 30, 2010, now Pat. No. 8,413,724.

(51) Int. Cl.
| | |
|---|---|
| *E21B 17/04* | (2006.01) |
| *E21B 43/01* | (2006.01) |
| *E21B 17/01* | (2006.01) |
| *A61N 1/362* | (2006.01) |
| *E21B 43/36* | (2006.01) |
| *A61N 1/368* | (2006.01) |

(52) U.S. Cl.
CPC .............. *E21B 17/01* (2013.01); *A61N 1/3627* (2013.01); *E21B 43/36* (2013.01); *A61N 1/3682* (2013.01)

(58) Field of Classification Search
CPC .......... E21B 17/01; E21B 17/10; E21B 43/36
USPC ............ 166/345, 357, 363, 367; 251/1.1, 1.2; 405/224.2
See application file for complete search history.

(56) References Cited

U.S. PATENT DOCUMENTS

| | | | | |
|---|---|---|---|---|
| 3,189,098 | A * | 6/1965 | Haeber | 166/352 |
| 3,280,908 | A * | 10/1966 | Todd | 166/340 |
| 3,858,401 | A * | 1/1975 | Watkins | 405/224.2 |
| 4,078,605 | A * | 3/1978 | Jones | 166/359 |
| 4,099,560 | A * | 7/1978 | Fischer et al. | 166/350 |
| 4,210,208 | A * | 7/1980 | Shanks | 166/352 |
| 4,374,595 | A * | 2/1983 | Watkins | 285/123.2 |
| 4,444,250 | A * | 4/1984 | Keithahn et al. | 166/84.4 |
| 4,456,062 | A * | 6/1984 | Roche et al. | 166/84.4 |
| 4,456,063 | A * | 6/1984 | Roche | 166/84.4 |
| 4,626,135 | A * | 12/1986 | Roche | 405/224.2 |
| 4,646,840 | A * | 3/1987 | Bartholomew et al. | 166/350 |
| 4,648,747 | A * | 3/1987 | Watkins et al. | 405/224.2 |
| 4,832,126 | A * | 5/1989 | Roche | 166/358 |
| 5,390,966 | A * | 2/1995 | Cox et al. | 285/124.2 |

(Continued)

*Primary Examiner* — Matthew Buck
(74) *Attorney, Agent, or Firm* — Bracewell & Giuliani LLP

(57) ABSTRACT

Method, riser assembly and gas handler for diverting gas from a riser. The riser assembly includes a riser having a first end and a second end and a conduit extending from the first end to the second end; a gas handler connected to the riser and provided between the first end and the second end, the gas handler having an external casing; plural pipes attached to an outside of the riser such that at least one pipe of the plural pipes enters through the external casing; and a gas vent pipe configured to start at the gas handler and extend towards the second end of the riser and the gas vent pipe is further configured to divert a gas from the gas handler through the outside of the riser.

16 Claims, 11 Drawing Sheets

(56) References Cited

U.S. PATENT DOCUMENTS

| | | | |
|---|---|---|---|
| 5,634,671 A * | 6/1997 | Watkins | 285/18 |
| 5,992,893 A * | 11/1999 | Watkins | 285/18 |
| 6,419,277 B1 * | 7/2002 | Reynolds | 285/123.1 |
| 6,470,975 B1 * | 10/2002 | Bourgoyne et al. | 175/57 |
| 6,623,044 B1 * | 9/2003 | Guesnon et al. | 285/124.1 |
| 6,637,513 B1 * | 10/2003 | van der Poel | 166/350 |
| 6,837,311 B1 * | 1/2005 | Sele et al. | 166/353 |
| 7,159,669 B2 * | 1/2007 | Bourgoyne et al. | 166/382 |
| 7,210,531 B2 * | 5/2007 | van Belkom et al. | 166/367 |
| 7,258,171 B2 | 8/2007 | Bourgoyne et al. | |
| 7,441,602 B2 * | 10/2008 | Saint-Marcoux | 166/302 |
| 7,497,266 B2 * | 3/2009 | Fossli | 166/358 |
| 7,762,337 B2 * | 7/2010 | Papon et al. | 166/345 |
| 8,037,939 B2 * | 10/2011 | Poirette et al. | 166/367 |
| 8,413,724 B2 * | 4/2013 | Carbaugh et al. | 166/345 |
| 2010/0270025 A1 * | 10/2010 | Larson et al. | 166/367 |
| 2012/0132432 A1 | 5/2012 | Carbaugh et al. | |

* cited by examiner

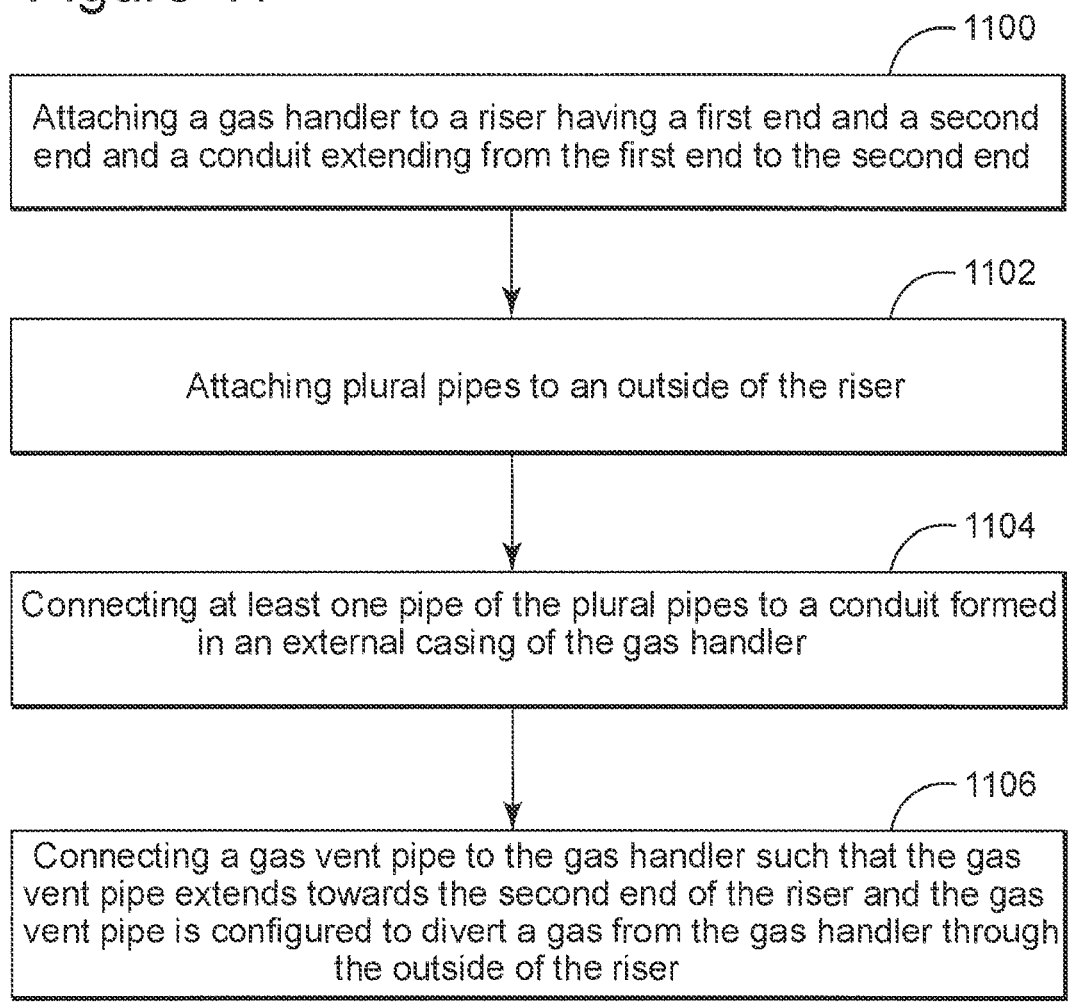

GAS HANDLER, RISER ASSEMBLY, AND METHOD

CROSS REFERENCE TO RELATED APPLICATIONS

This application is a divisional of, and claims priority to and the benefit of, U.S. patent application Ser. No. 12/956,218, which was filed Nov. 30, 2010, the full disclosure of which is hereby incorporated herein by reference.

BACKGROUND OF THE INVENTION

1. Field of the Invention

Embodiments of the subject matter disclosed herein generally relate to methods and systems and, more particularly, to mechanisms and techniques for subsea drilling.

2. Brief Description of Related Art

During the past years, with the increase in price of fossil fuels, the interest in developing new production fields has dramatically increased. However, the availability of land-based production fields is limited. Thus, the industry has now extended drilling to offshore locations, which appear to hold a vast amount of fossil fuel.

However, a problem posed by the underwater exploration, and especially deep water exploration, is the control of gas in the marine riser. The marine riser (or a lower marine riser package) is essentially a pipe made of many components that connects a rig or vessel that floats at the surface of the water to a blowout preventer provided undersea at a well head. These elements are shown in FIG. 1. More specifically, an oil and gas exploration system 10 includes a vessel (or rig) 12 having a reel 14 that supplies power/communication cables 16 to a controller 18. The controller 18 is disposed undersea, close to or on the seabed 20. In this respect, it is noted that the elements shown in FIG. 1 are not drawn to scale and no dimensions should be inferred from FIG. 1.

FIG. 1 also shows that a drill string 24 is provided inside a riser system 40, that extends from vessel 12 to one or more BOPs 26 and 28. A wellhead 22 of the subsea well is connected to a casing 44, which is configured to accommodate the drill string 24 that enters the subsea well. At the end of the drill string 24 there is a drill bit (not shown). Various mechanisms, also not shown, are employed to rotate the drill string 24, and implicitly the drill bit, to extend the subsea well. The dirt and debris produced by the drill string 24 are removed by circulating a special fluid, called "mud", through an inside of the drill string 24 and then through an annulus formed between the outside of the drill string 24 and an inside of the riser system 40. Thus, the mud is pumped from the vessel 12 through the drill string 24 down to the drill bit and back through the annulus of the riser system 40 back to the vessel 12.

The riser system 40 is currently installed in the following way. The vessel 12 stores plural risers that may be connected one to the other to form the riser system 40. Each riser is lowered through a deck of the vessel 12, substantially perpendicular to the surface of the water. Once a first riser is immersed into the water, a second riser is attached to the first riser and further immersed into the water. The process goes on until the first riser reaches the equipment at the well head. At that stage, the first riser is secured to the equipment. Thus, each riser has to have an external diameter less than an internal diameter of a hole in the deck or otherwise the riser cannot be lowered through the deck of vessel 12.

Conventionally, plural pipes are attached to an outside of the riser, e.g., choke line, kill line, blue conduit, yellow conduit, etc. and form a riser assembly. Also, in order to prevent a possible gas bubble to propagate from the well to the vessel, a gas handler may be attached to at least a riser assembly of the riser system 40. Such a riser assembly 50 having a riser 51 with a gas handler 52 is shown in FIG. 2. The riser 51 has a top end 54a and a lower end 54b configured to connect to other risers. FIG. 2 also shows the various lines (pipes) 56a to 56d that run along an outside of the riser 50. Because of the size limitations of the deck of the vessel, FIG. 2 shows that the lines 56a to 56d are bent and provided at a single side 58 of the gas handler 52 in order to reduce an overall exterior diameter of the riser assembly 50 to fit through the deck.

However, from a manufacturing point of view, bending the pipes 56a to 56d as shown in FIG. 2 is time consuming and adds to the overall cost of the riser assembly. Accordingly, it would be desirable to provide systems and methods that avoid the afore-described problems and drawbacks.

SUMMARY OF THE INVENTION

According to one exemplary embodiment, there is a riser assembly to be used in underwater oil and gas exploration. The riser assembly includes a riser having a first end and a second end and a conduit extending from the first end to the second end; a gas handler connected to the riser and provided between the first end and the second end, the gas handler having an external casing; plural pipes attached to an outside of the riser such that at least one pipe of the plural pipes enters through the external casing; and a gas vent pipe configured to start at the gas handler and extend towards the second end of the riser and the gas vent pipe is further configured to divert a gas from the gas handler through the outside of the riser.

According to another exemplary embodiment, there is a gas handler configured to remove gas from a riser. The gas handler includes an external casing having first and second ends; a wall provided inside the external casing and configured to define an elongated cavity; a piston configured to move along the elongated cavity; a sleeve configured to move along the elongated cavity, wherein the piston and the sleeve are provided in a chamber around the elongated cavity; an elastomeric body configured to be pressed by the piston to close the elongated cavity; a gas vent conduit formed in a wall of the external casing and configured to output the gas; and a conduit formed in a wall of the external casing and configured to extend from the first end to the second end.

According to still another exemplary embodiment, there is a method for assembling a riser assembly. The method includes attaching a gas handler to a riser having a first end and a second end and a conduit extending from the first end to the second end; attaching plural pipes to an outside of the riser; connecting at least one pipe of the plural pipes to a conduit formed in an external casing of the gas handler; and connecting a gas vent pipe to the gas handler such that the gas vent pipe extends towards the second end of the riser and the gas vent pipe is configured to divert a gas from the gas handler through the outside of the riser.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 11 is a flow chart of a method for assembling a riser assembly according to an exemplary embodiment.

DETAILED DESCRIPTION OF THE PREFERRED EMBODIMENT

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of risers, riser assemblies, and riser systems. However, the embodiments to be discussed next are not limited to these systems, but may be applied to other systems that require to have an overall exterior diameter less than a predetermined size.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an exemplary embodiment, a gas handler that is provided on a riser is configured to receive plural pipes such that the plural pipes do not have to be bent around and brought to one side of the body. In one application, all the plural pipes enter through a housing of the gas handler in order to pass the gas handler.

Figure 1:
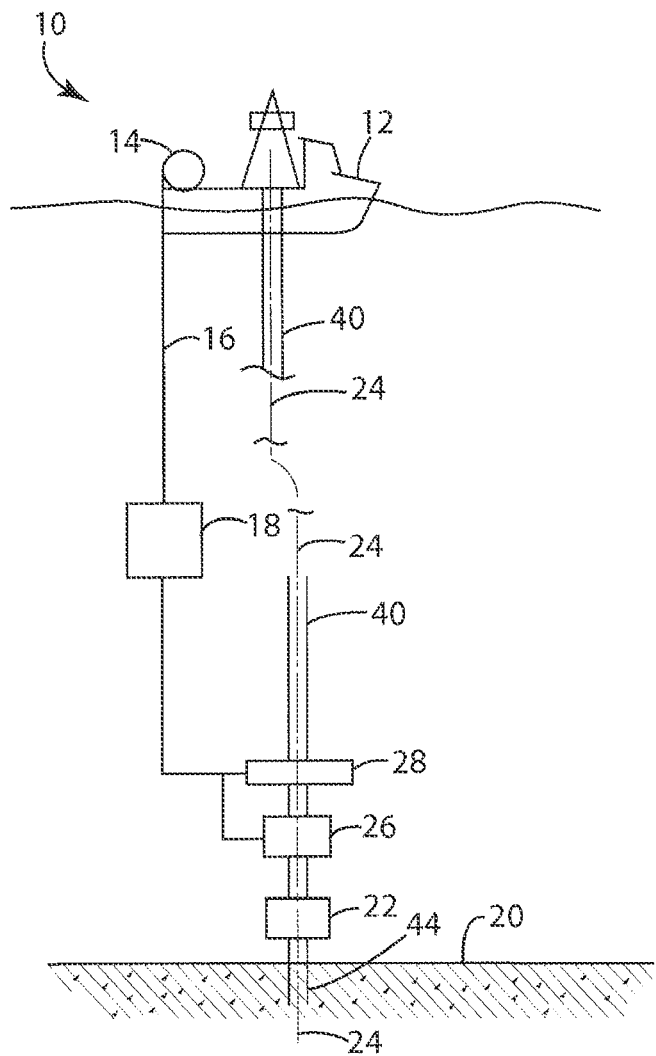
FIG. 1 is a schematic diagram of a conventional offshore rig.
Figure 2:
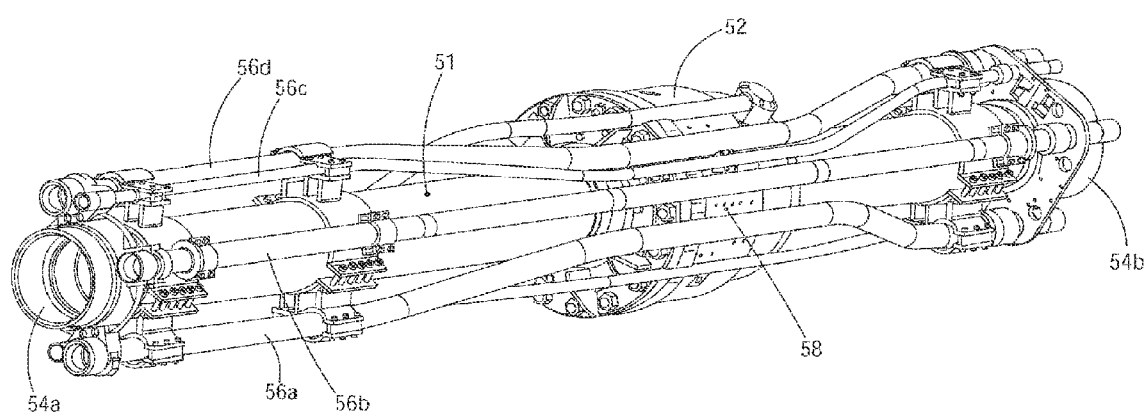
FIG. 2 is a schematic diagram of a conventional riser assembly with a gas handler.
Figure 3:
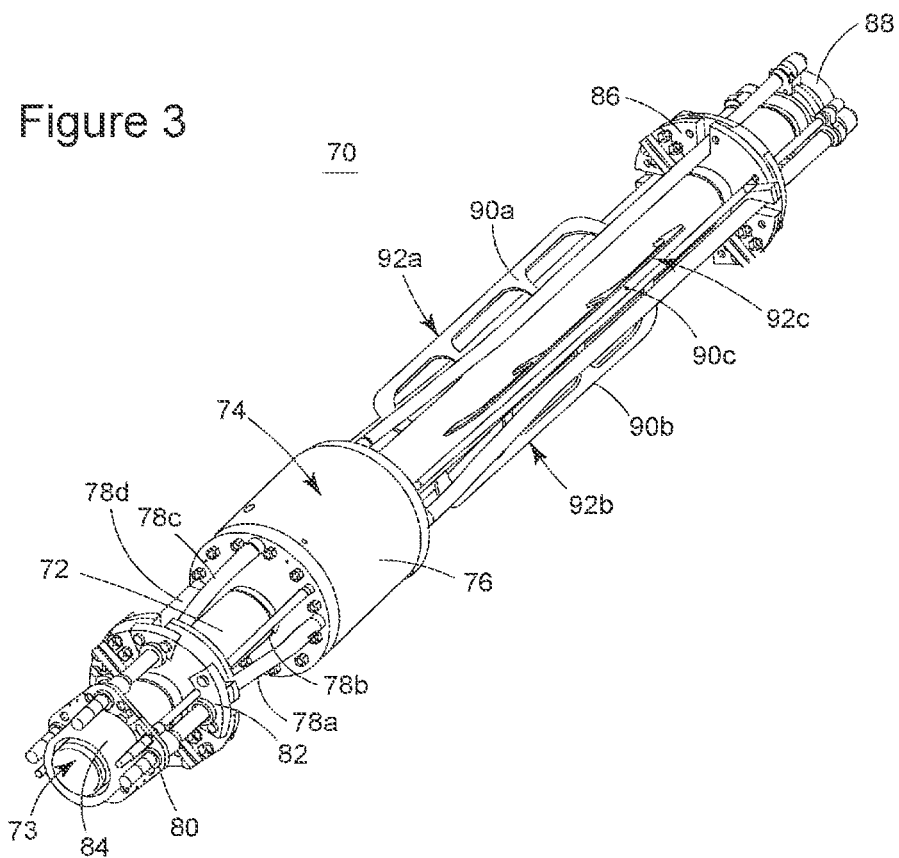
FIG. 3 is a schematic diagram of a riser assembly having a novel gas handler according to an exemplary embodiment.

According to an exemplary embodiment illustrated in FIG. 3, a riser assembly 70 includes a riser 72 and a gas handler 74. The gas handler 74 has an external casing 76 having a predetermined external diameter. The external diameter of the external casing 76 is smaller than a diameter of a hole in a deck through which the riser assembly has to pass. Plural pipes 78a-d are provided outside the riser 72 and attached to riser 72 by brackets 80. An imaginary cylinder that includes all the pipes has a diameter smaller than the external diameter of the casing 76. A guide bracket 82 may be placed at a bottom end 84 of the riser 72 and another guide bracket 86 may be placed at a top end 88 of the riser 72. The bottom and top ends of the riser are defined relative to a position of the riser when provided in the riser system underwater. Other risers are configured to be attached to ends 84 and 88 of the current riser 72. The riser 72 has a conduit 73 that extends from the bottom end 84 to the top end 88 and this conduit is configured to receive a drill line (not shown).

The guide brackets 82 and 86 are used for aligning the plural pipes 78a-d when assembled and holding them secure during pressurization. More or less guide brackets may be used. The plural pipes 78a-d may include a mud boost line, a choke line, a kill line, a yellow conduit line, a blue conduit line. Other lines are also possible. FIG. 3 also shows plural bumper plates 90a-c that are attached to the riser 72. The bumper plates are provided between the plural pipes 78a-d and have corresponding edges 92a-c configured to be more elevated than the plural pipes relative to an outer surface of the riser 72. In this way, when the riser assembly 70 is lowered through the deck of the vessel, the plural pipes do not bump into the edges of the deck. It is noted that due to the continuous movement of the vessel (waves, etc.), when the riser assembly is lowered through the deck, the riser assembly is prone to moving and thus hitting the edges of the deck. Thus, the bumper plates protect the plural pipes from being deformed during such interactions with the deck.

Figure 4:
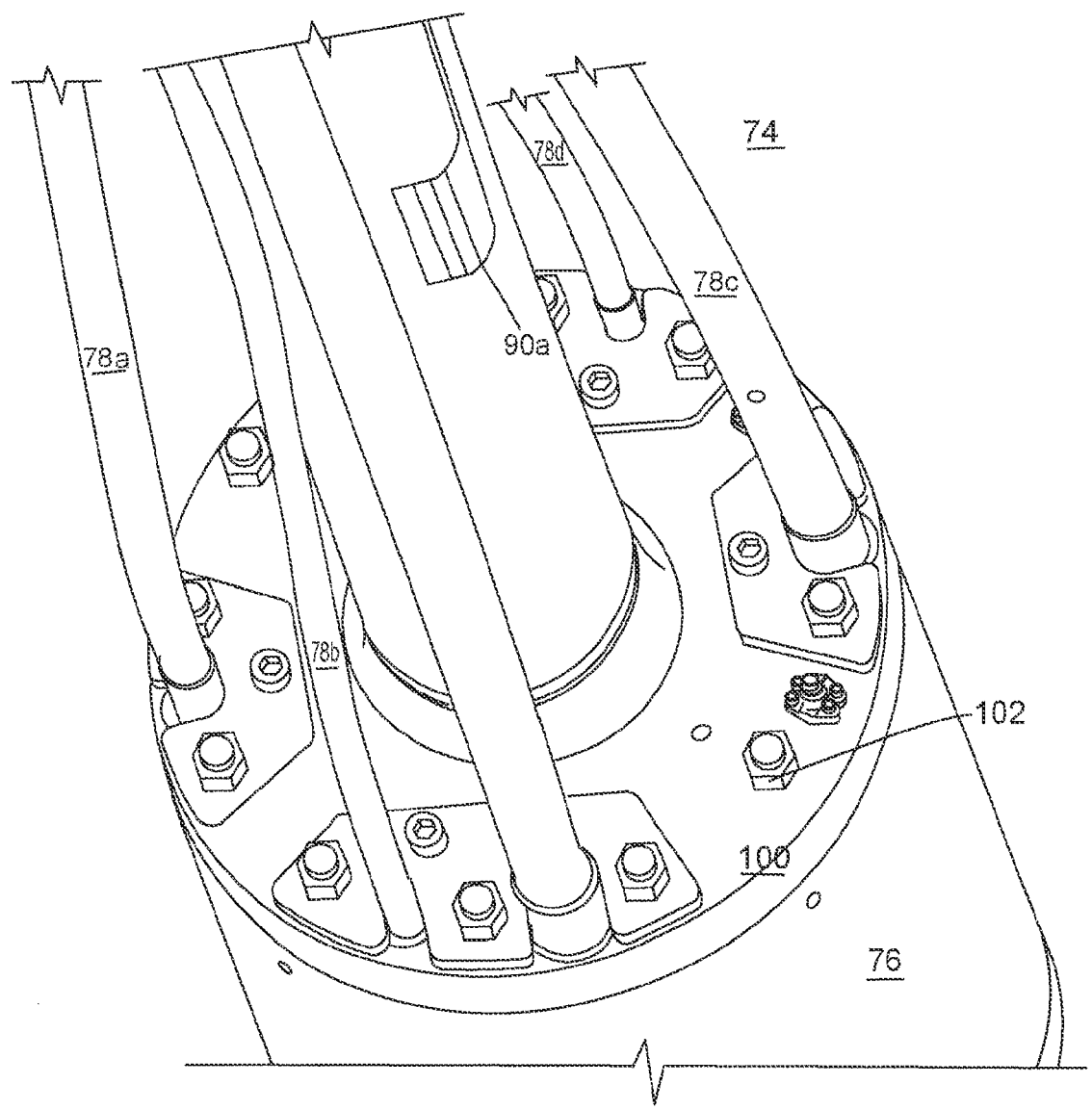
FIG. 4 is a schematic diagram of a cap of a gas handler according to an exemplary embodiment.
Figure 5:
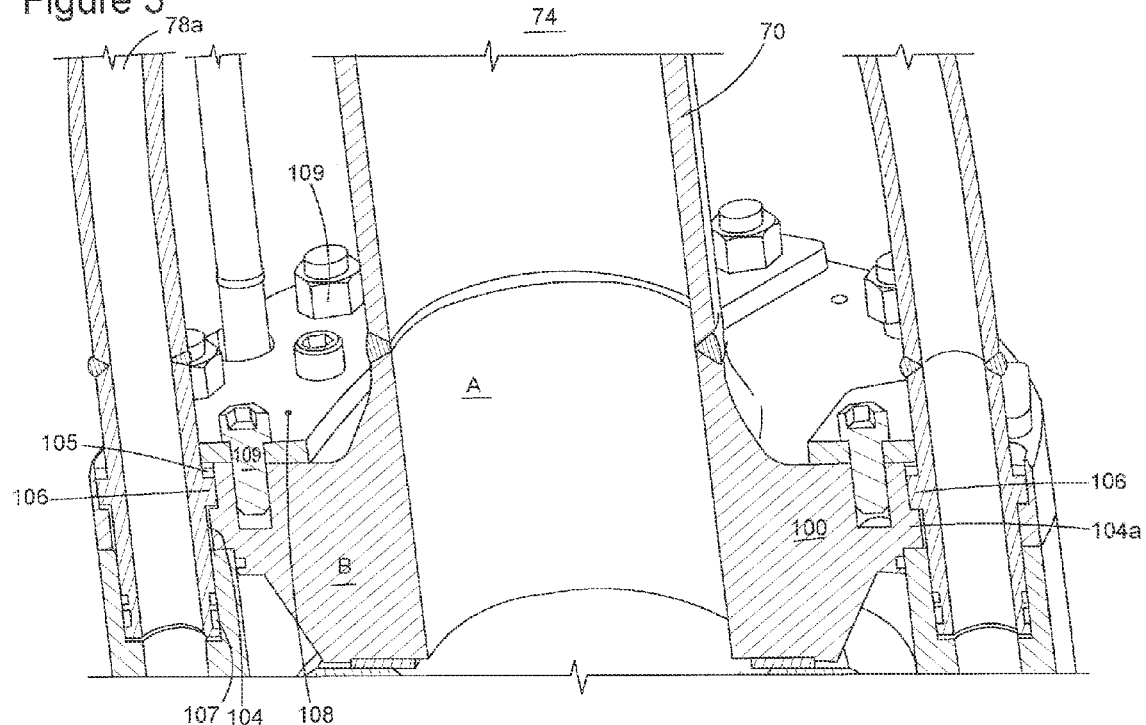
FIG. 5 is a schematic diagram of a line entering a cap of a gas handler according to an exemplary embodiment.

According to an exemplary embodiment illustrated in FIG. 4, a more detailed view of the connection between the plural pipes 78a-d and the gas handler 74 is presented. The casing 76 has an upper cap 100 that may be attached with bolts 102 to the casing 76. A pipe 78a is configured to enter through the upper cap 100 via a hole (not shown). Each pipe of the plural pipes 78a-d may have a corresponding hole in the cap 100. FIG. 5 shows the hole 104 of the cap 100. FIG. 5 also shows that pipe 78a has a collar 106 or other means (a shoulder) that is configured to be accommodated by hole 104. The collar 106 may be welded to the pipe 78a. Each pipe 78a-d may have a similar collar. The hole 104 may have a shoulder 104a for preventing the pipe 78a to further enter into the casing 76.

For maintaining the pipe 78a in place, i.e., inside the gas handler 74, a plate 108 is configured to be attached to the cap 100, around the pipe 78a. In this way, the collar 106 is prevented to exit the hole 104 and the pipe 78a is secured to the cap 100. An appropriate seal or washer 105 may be used between the collar 106 and the plate 108. Plate 108 is secured to upper cap 100 by bolts 109. One or more seals 107 may be used between the pipe 78a and the hole 104 for preventing a fluid inside the pipe 78a from escaping. According to an exemplary embodiment, the pipe 78a may enter through the cap 100 to reach the casing 76.

Figure 6:
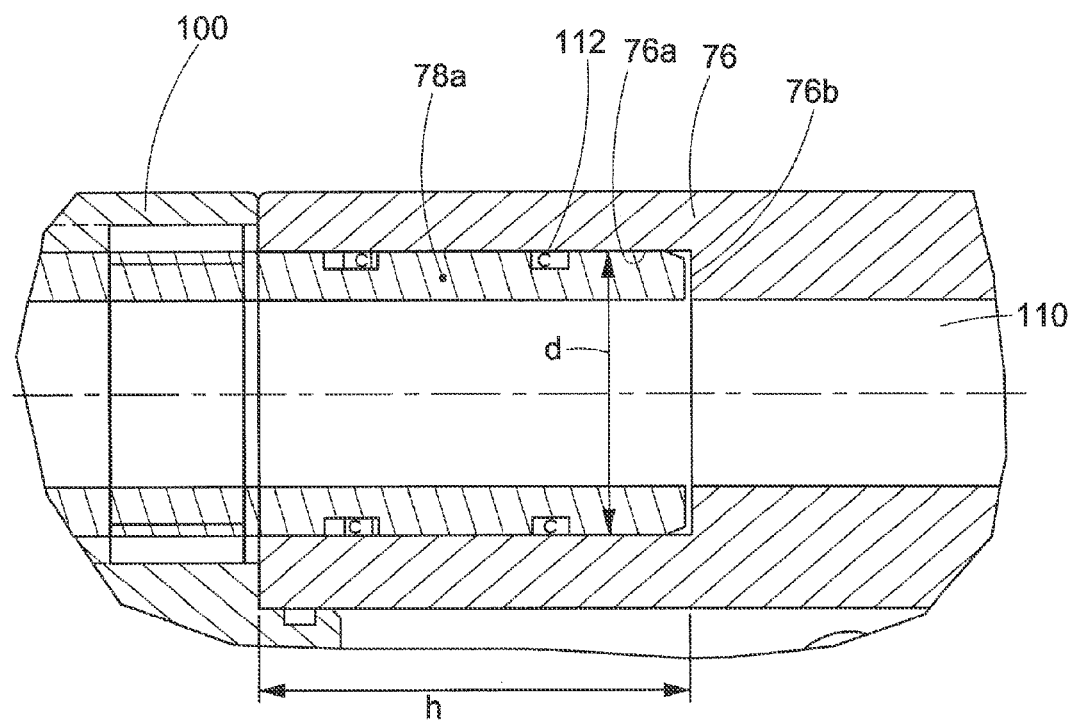
FIG. 6 is a schematic diagram of a line entering a casing of a gas handler according to an exemplary embodiment.

The pipe 78a ends inside the casing 76 as shown in FIG. 6. In other words, a conduit 110 is formed through the casing 76, from one end to the other, for transmitting the fluid under pressure across the gas handler 74. For achieving this goal, the casing 76 is configured to have a receptacle region 76a having an inner diameter d that fits (plus normal tolerances) an outer diameter of the pipe 78a. Receptacle region 76a has an upward facing receptacle shoulder 76b. The pipe 78a may be stabbed into the receptacle 76a. For ensuring that no pressure from inside the pipe 78a escapes outside, plural seals 112 may be provided at an interface between the pipe 78a and the receptacle 76a. The pipe 78a may enter a predetermined depth h into the casing 76. A similar arrangement may be provided at the other end of the casing 76 for a corresponding part. Returning to FIG. 5, the riser 70 may be attached to the cap 100 either by welding or by forming the riser 70 integrally with and the cap 100.

Figure 7:
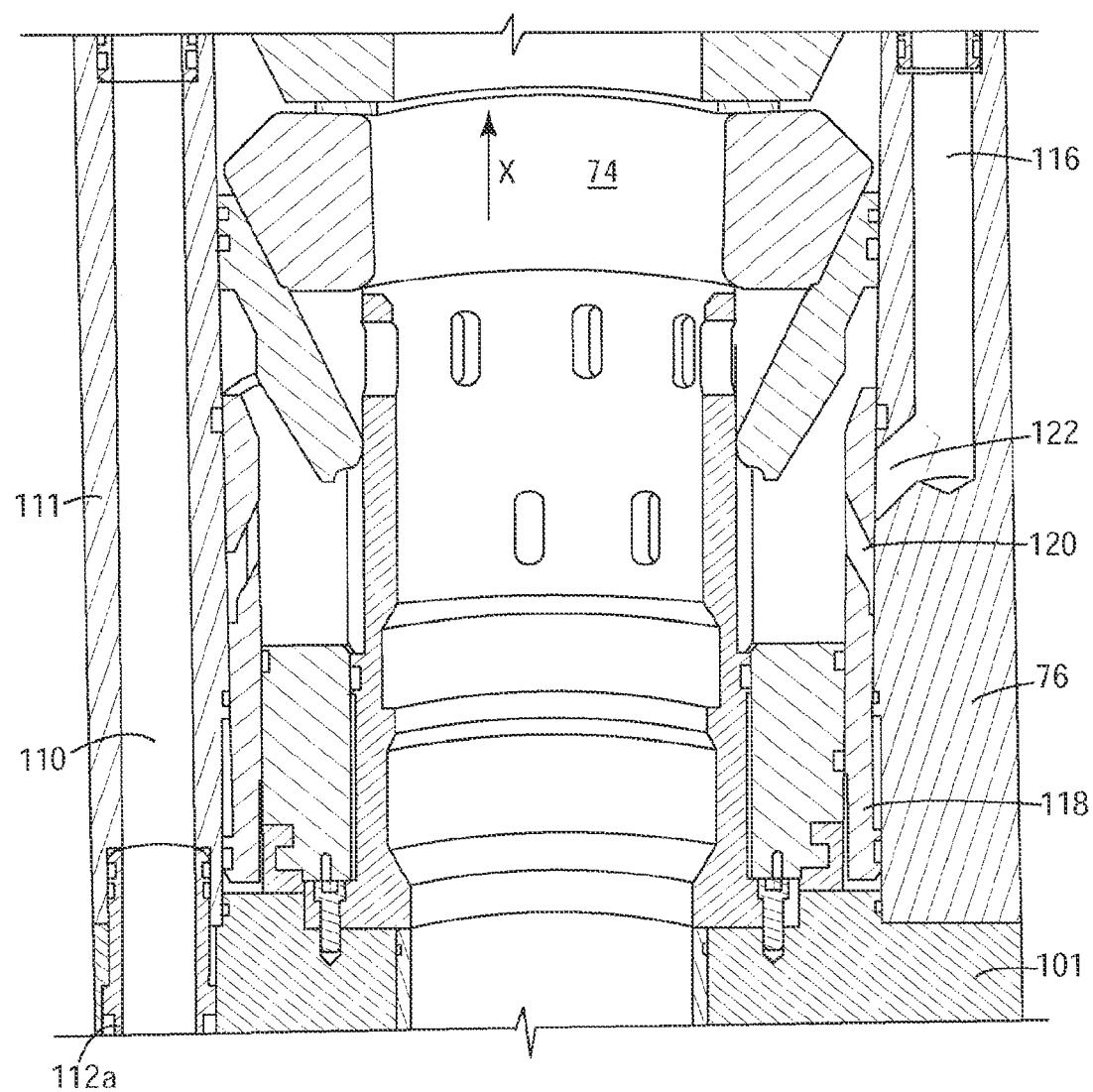
FIG. 7 is a schematic diagram of an interior of a gas handler according to an exemplary embodiment.

The gas handler 74 is discussed now with reference to FIG. 7. The gas handier 74 has the exterior casing 76 formed to incorporate most if not all of its components. In one application, the exterior casing 76 is a cylinder. FIG. 7 shows a lower cap 101 that is attached, similar to the upper cap 100, to the casing 76. FIG. 7 also shows the conduit 110 formed through a wall 111 of the casing 76, from the upper cap 100 to the lower cap 101. A pipe 112a enters through the lower cap 101 and partially into the casing 76 to fluidly communicate with the conduit 110. The pipe 112a corresponds to the pipe 78a and together they form, for example, the kill line or any other line.

The gas handler 74 is configured to remove gas under pressure that might appear inside the riser 70. If the gas under pressure is not removed from the riser, that gas might make its way to the vessel with catastrophic consequences, e.g., explosion. For this reason, the gas handler 74 is an important safety device of the subsea exploration system. The gas that is captured by the gas handler 74 has to be removed from the riser 70 and delivered, in a safety way, to a desired location. For example, the gas might be delivered at the surface of the water, away from the vessel. For this reason, a gas vent conduit 116 is formed in the wall of the casing 76 as shown in FIG. 7. The gas vent conduit 116 is configured to communicate with a sleeve 118 that has a passage 120. As shown in FIG. 7, the sleeve 118 fully closes the gas vent conduit 116 by misaligning the passage 120 with a corresponding port 122 of the gas vent conduit 116. In this position, no gas can escape from the riser via the gas vent conduit 116.

Figure 8:
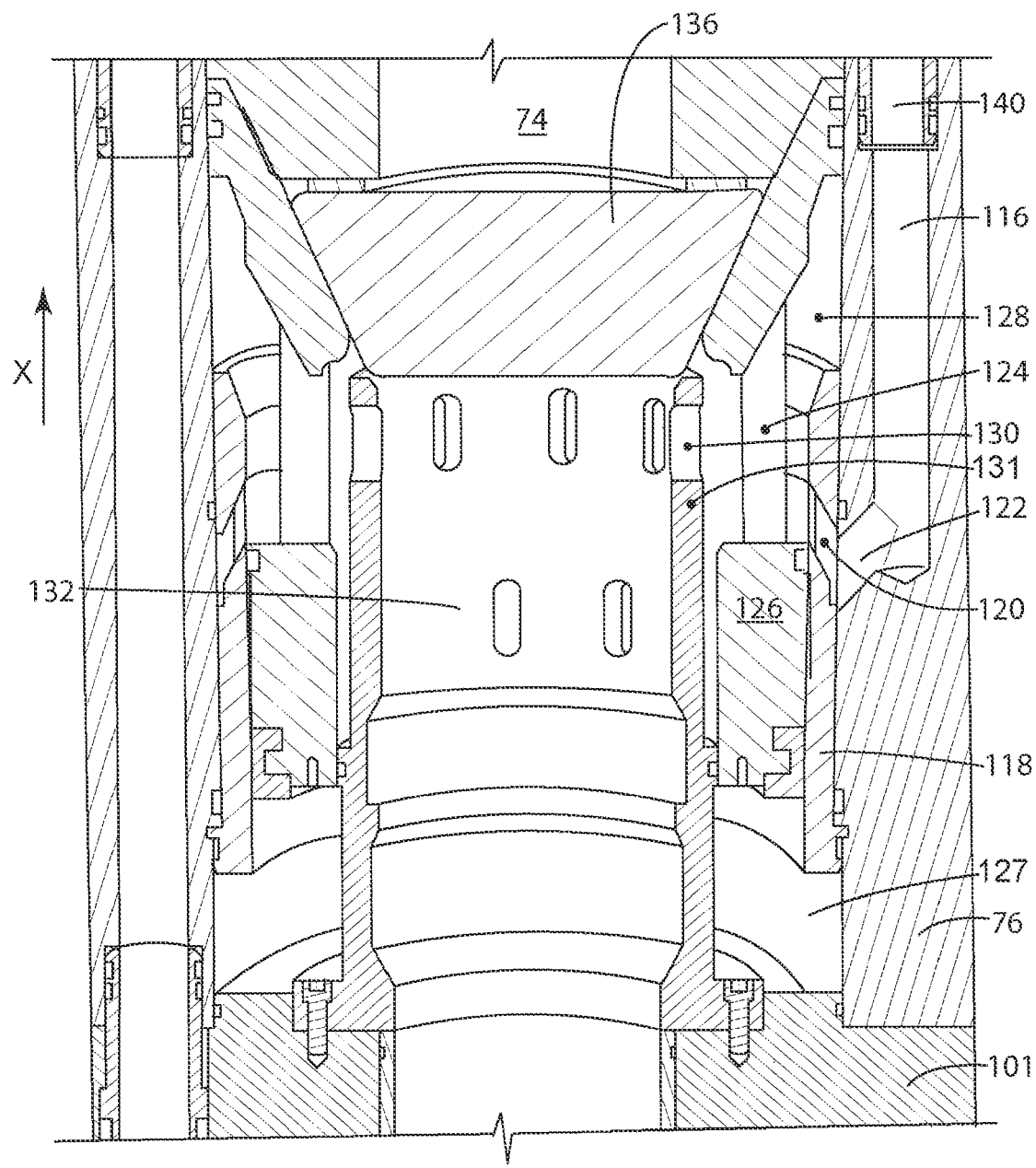
FIG. 8 is an schematic diagram of a closed piston of a gas handler according to an exemplary embodiment.

However, the sleeve 118 may be moved upwards (along axis X), along a direction of the riser, as shown in FIG. 8. In the embodiment shown in FIG. 8, the port 122 of the gas vent conduit 116 is in fluid communication with the passage 120 of the sleeve 118. Further, a gas from inside the riser may travel through an opening 124 of a piston 126 to be discussed later. The piston 126 and the sleeve 118 are provided in a chamber 127 of the gas handler 74. The piston 126 and the sleeve 118 are configured to move along axis X as desired by an operator of the well. The gas from the riser 72 may travel to the gas vent conduit 116 as a cavity 128 is provided at an interface between the sleeve 118 and the piston 126. FIG. 8 also shows a hole 130 (in reality may be plural holes 130) in a wall 131 that defines a cavity 132. The cavity 132 fluidly connects two parts (above and below the gas handler) of the riser 72 and the hole 130 fluidly communicates the cavity 132 (e.g., inside of the riser 72) with the chamber 127. The cavity 132 may be elongated along the axis X, e.g., have a cylindrical shape.

Under certain circumstances, it is possible that the piston 126 moves upwards as also shown in FIG. 8 for pressing an elastomer body 136 for closing the communication between the two parts of the riser 70. When this is happening, the gas propagating through the riser is stopped at the gas handler 74 and this gas is provided to the gas vent conduit 116 via the hole 130, opening 124, cavity 128, passage 120, and port 122. This gas further propagates from the gas vent conduit 116 to a gas vent line 140 towards the vessel above. The gas vent line 140 may be connected to the gas vent conduit 116 in a similar manner as the line 78a is connected to conduit 110.

Figure 9:
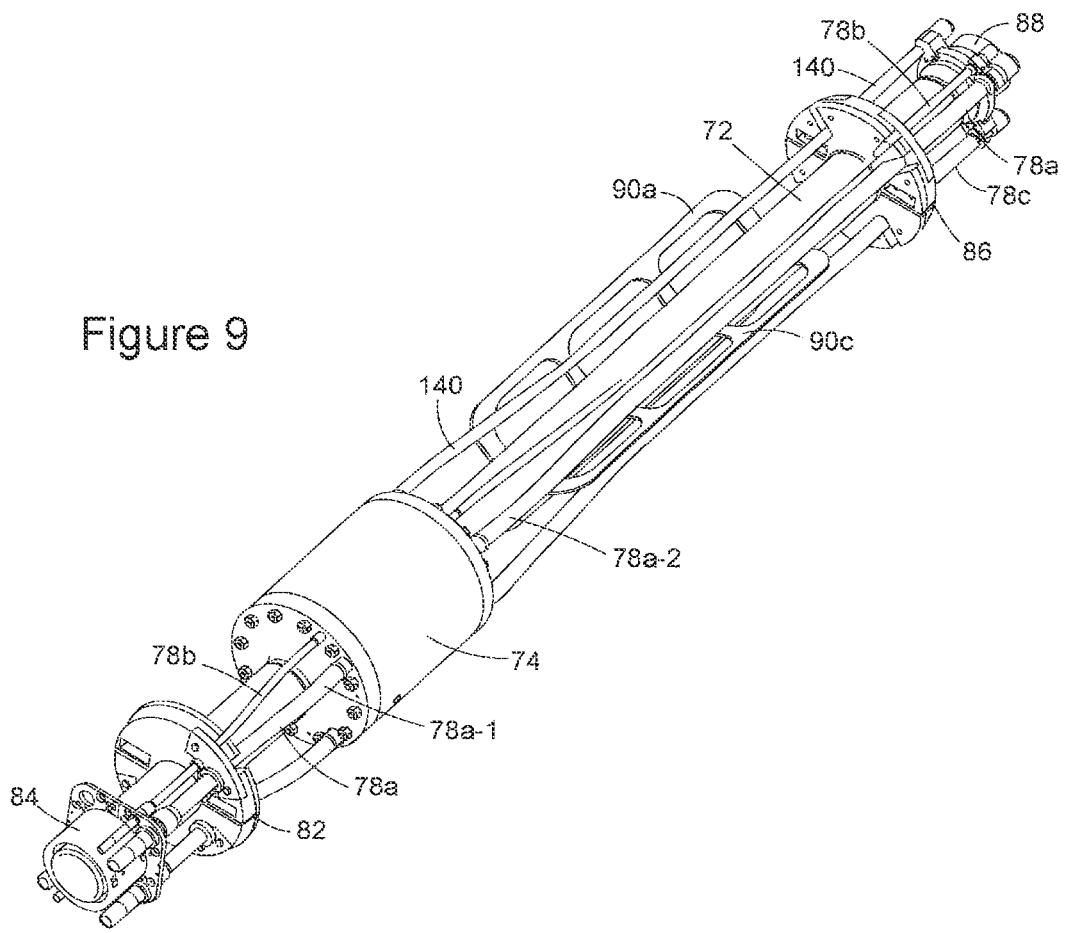
FIG. 9 is a schematic diagram of a riser assembly according to an exemplary embodiment.
Figure 10:
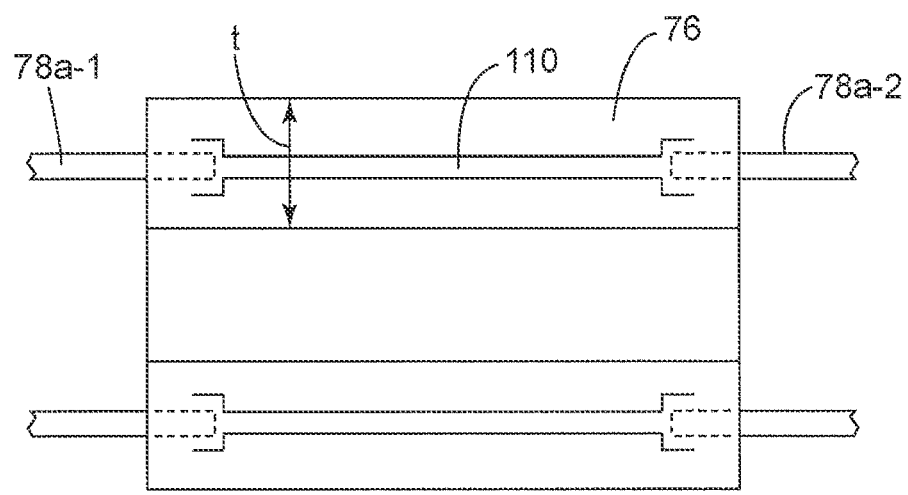
FIG. 10 is a schematic diagram of a cut-through of a gas handler according to an exemplary embodiment.

The gas vent line 140 is shown in FIG. 9 together with the other lines. It is noted that the gas vent line extends from the gas handler 74 only towards the upper end 88 of the riser 72 and not towards the lower end 84 of the riser 72. Thus, the gas vent line 140 is different from the other lines 78a-d as this line originates at the gas handler 74. Further, it is noted that any of the lines 78a-d may be formed from two portions that are not in direct contact to each other. For example, line 78a may have a first portion 78a-1 and a second portion 78a-2. These two portions are in fluid communication with each other but not in direct contact with each other as shown in FIG. 10. FIG. 10 shows a cross-section through the gas handler 74 with the external casing 76 having a given thickness "t". In the external casing, the conduit 110 is formed and the conduit 110 connects the first portion 78a-1 of the line 78a to the second portion 78a-2 of the same line 78a. The same may be true for the other lines 78b-d. However, in another application, the conduit 110 may be formed not in the wall of the casing 76 but inside the casing 76.

According to an exemplary embodiment illustrated in FIG. 11, there is a method for assembling a riser assembly. The method includes a step 1100 of attaching a gas handler (74) to a riser (72) having a first end (84) and a second end (88) and a conduit (73) extending from the first end (84) to the second end (88); a step 1102 of attaching plural pipes (78a-d) to an outside of the riser (72); a step 1104 of connecting at least one pipe (78a) of the plural pipes (78a-d) to a conduit (110) formed in an external casing (76) of the gas handler (74); and a step 1106 of connecting a gas vent pipe (140) to the gas handler (74) such that the gas vent pipe (140) extends towards the second end (88) of the riser (72) and the gas vent pipe (140) is configured to divert a gas from the gas handler (74) through the outside of the riser (72).

The disclosed exemplary embodiments provide a system and a method for streamlining an oil and gas exploration process in which a riser system is used to connect an undersea well to a vessel. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A gas handler for use with a riser assembly, comprising:
an external casing having a central passage;
an elastomeric body surrounding the passage that is movable by a piston to a closed position blocking upward flow through the central passage;
a gas vent conduit in fluid communication with the central passage;
a valve sleeve that selectively blocks and opens fluid communication between the central passage and the gas vent conduit;
a gas vent pipe configured to start at the gas vent conduit of the gas handler, and to divert a gas away from the gas handler; and
a plurality of pipes having flow paths that pass through the external casing of the gas handler alongside the central passage.

2. The gas handler of claim 1, wherein the gas vent pipe extends upwardly towards the upper end of the riser assembly.

3. The gas handler of claim 1, wherein an external diameter of the casing is larger than a diameter of an imaginary cylinder that encompasses the plurality of pipes.

4. The gas handler of claim 1, wherein the plurality of pipes include a choke line, a kill line, and hydraulic fluid conduits.

5. A gas handler for use with a riser assembly, comprising:
an external casing;
a plurality of pipes configured so that at least one pipe of the plurality of pipes enters through the external casing, the at least one pipe made of a first portion and a second portion that are not in direct contact with each other;
a gas vent pipe configured to start at the gas handler, and to divert a gas away from the gas handler; and
a lower cap and an upper cap configured to be attached to the external casing.

6. The gas handler of claim 5, wherein the first portion enters through the lower cap and the second portion enters through the upper cap and a conduit formed in a wall of the external casing fluidly communicates the first portion with the second portion.

7. The gas handler of claim 5, further comprising a receptacle region provided in the upper cap for receiving the at least one pipe, the receptacle region being configured to partially enter into a wall of the external casing of the gas handler and to fluidly communicate with a conduit formed in a wall of the external casing of the gas handler.

8. The gas handler of claim 7, wherein a portion of the at least one pipe has a collar configured to enter into the receptacle region.

9. The gas handler assembly of claim 7, further comprising at least one seal between the receptacle region and the external casing for preventing a fluid inside the at least one pipe to escape outside.

10. A gas handler configured to remove gas from a riser, the gas handler comprising:
an external casing having first and second ends;
a wall provided inside the external casing and configured to define an elongated cavity;
a piston configured to move along the elongated cavity;
a sleeve configured to move along the elongated cavity, wherein the piston and the sleeve form a chamber for hydraulic control fluid around the elongated cavity;
an elastomeric body configured to be pressed by the piston to close the elongated cavity;
a gas vent conduit formed in a wall of the external casing and configured to output the gas; and
a conduit formed in a wall of the external casing and configured to extend from the first end to the second end.

11. The gas handler of claim 10, further comprising:
a first cap configured to be attached to the external casing at the first end; and
a second cap configured to be attached to the external casing to the second end.

12. The gas handler of claim 11, further comprising:
a receptacle region provided in the first cap or the second cap and partially into the wall of the external casing, wherein the receptacle region is configured to receive a pipe, external to the gas handler, and to fluidly connect the pipe to the conduit.

13. The gas handler of claim 11, wherein at least one pipe is made of a first portion and a second portion that are not in direct contact with each other and the first portion enters through the first cap and the second portion enters through the second cap and the conduit formed in the wall of the external casing fluidly communicates the first portion with the second portion.

14. The gas handler of claim 10, further comprising:
a receptacle region provided in the external casing for receiving at least one pipe, the receptacle region being configured to partially enter into the wall of the external casing of the gas handler and to fluidly communicate with the conduit formed in the wall of the external casing of the gas handler.

15. The gas handler of claim 14, wherein a portion of the at least one pipe has a collar configured to enter into the receptacle region.

16. The gas handler of claim 14, further comprising:
at least one seal between the receptacle region and the external casing for preventing a fluid inside the at least one pipe to escape outside.

* * * * *